US009125745B2

(12) United States Patent
Deshpande (10) Patent No.: US 9,125,745 B2
(45) Date of Patent: Sep. 8, 2015

(54) APPARATUS AND METHOD FOR AIRWAY PATENCY AND HEAD IMMOBILIZATION

(75) Inventor: Girish G. Deshpande, Peoria, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 532 days.

(21) Appl. No.: 12/577,584

(22) Filed: Oct. 12, 2009

(65) Prior Publication Data

US 2010/0089410 A1     Apr. 15, 2010

Related U.S. Application Data

(60) Provisional application No. 61/104,939, filed on Oct. 13, 2008.

(51) Int. Cl.
*A61B 19/00* (2006.01)
*A61F 5/37* (2006.01)
*A61G 13/12* (2006.01)

(52) U.S. Cl.
CPC ............ *A61F 5/3707* (2013.01); *A61G 13/121* (2013.01); *A61G 13/1215* (2013.01)

(58) Field of Classification Search
CPC .......... A61F 5/3707; A61F 5/37; A61F 5/56; A61G 13/121; A61G 13/1215; A61G 13/122
USPC ........ 128/97.1, 845, 846, 848, 857, 869, 870, 128/DIG. 23, 859, 876; 601/41–44; 602/18, 602/32, 33, 35, 36, 902, 17; 5/631, 632, 5/636, 637, 630, 640, 643, 625, 652, 5/628; 27/25.1, 13, 845; 2/10, 468; 297/391
See application file for complete search history.

(56) References Cited

U.S. PATENT DOCUMENTS

| | | | | | |
|---|---|---|---|---|---|
| 2,796,866 | A | * | 6/1957 | Cohen | 128/869 |
| 4,252,113 | A | * | 2/1981 | Scire | 5/628 |
| 4,267,830 | A | * | 5/1981 | Vick | 602/19 |
| 5,154,186 | A | * | 10/1992 | Laurin et al. | 5/625 |
| 5,515,869 | A | * | 5/1996 | Powell et al. | 5/628 |
| 5,524,639 | A | * | 6/1996 | Lanier et al. | 5/630 |
| 7,055,524 | B1 | * | 6/2006 | Taimoorazy | 128/845 |
| 2007/0118060 | A1 | | 5/2007 | Gefen et al. | |
| 2009/0133702 | A1 | * | 5/2009 | Chang | 128/870 |

OTHER PUBLICATIONS

Davis, et al., Team #4—Design of a Neck and Jaw Support Mechanism for Infants (Powerpoint presentation, date unknown).
Davis, et al., Team #4—Design of a Jaw Support Mechanism (Apr. 2009).
Hand, et al., Team #4—Design of Jaw Support Mechanism (May 2009).

* cited by examiner

*Primary Examiner* — Victoria J Hicks
(74) *Attorney, Agent, or Firm* — McDonnell Boehnen Hulbert & Berghoff LLP (57) ABSTRACT

A jaw-thrust device includes a base with an extension arm disposed on each side of a patient's head mounted on the base. A mandible rest is mounted on each extension arm such that the mandible rest may be deployed proximate to a patient's mandible. A chin pad and at least one connector connects the chin strap to at least one of the base or extension arm; whereby jaw thrusting pressure on the mandible rests causes rotational force on the chin straps such that the patient's mouth opens without substantially tilting the patient's head. The device maintains an open airway unattended.

20 Claims, 8 Drawing Sheets

APPARATUS AND METHOD FOR AIRWAY PATENCY AND HEAD IMMOBILIZATION

CROSS-REFERENCE TO RELATED APPLICATIONS

This application claims priority to U.S. Provisional Patent application No. 61/104,939 filed Oct. 13, 2008.

BACKGROUND OF THE INVENTION

1. Field of the Invention

The present invention is in the field of emergency medicine and particularly relates to airway maintenance.

2. Related Art

Establishing and maintaining a patient airway is one of the most important components of Basic Life Support (BLS). When patient loses consciousness, the muscles of the jaw and pharynx relax, tongue falls back and this results in obstruction of the airway. Obstructed airway will result in hypoxemia and hypercarbia from hypoventilation thus further worsening patient's condition.

Figure 1:
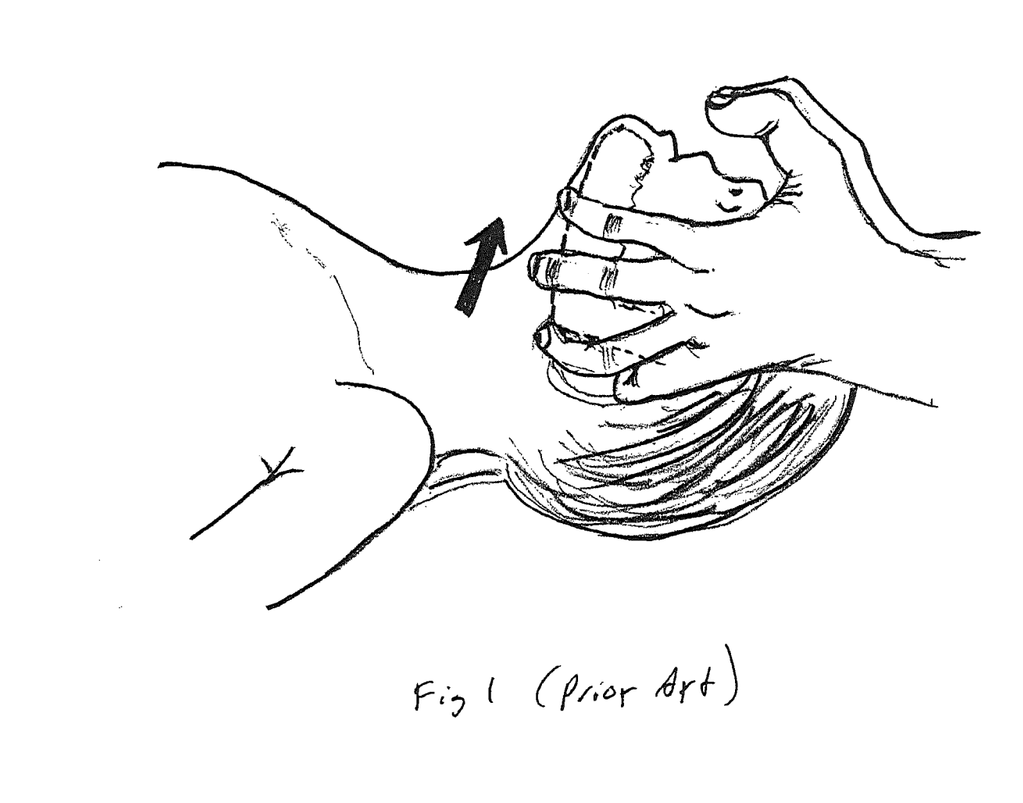
FIG. 1 is a side view of a manual jaw thrust.

Normally, a head tilt-chin lift maneuver is commonly performed to open an airway in unresponsive victims. However, in patients with suspected neck/cervical spinal injury, a jaw-thrust maneuver without head tilt is the recommended method of opening an airway, in order to keep the spine stable, as depicted in FIG. 1.

The jaw-thrust is very commonly used by medical personnel working in acute care settings such as EMT (Emergency Medical Technicians), emergency room physicians, intensivists and anesthesiologists. It may also be indicated in other situations such as post anesthesia. However, whenever someone is assisting in jaw-thrust maneuver he/she has to be completely focused on the airway and is usually unable to contribute to resuscitation. Thus these maneuvers result in tying up a person for the duration of time, until a permanent airway is established e.g., by intubation or until patient's consciousness has recovered enough to maintain airway by him/herself. A mechanical device, which will perform a jaw-thrust and chin-lift will be a reasonable solution and can be applied in various settings.

SUMMARY OF THE INVENTION

The present invention will advantageously: perform jaw-thrust and chin-tilt (instead of chin-lift) to open and maintain an airway for the duration of emergency or surgical care, be applicable to different age groups and sizes of the patient, be easy to apply and disconnect to and from the patient (user friendly), could be used in a variety of different settings by various users, be easy to clean and maintain, and be safe for patients of different ages and sizes.

Figure 2:
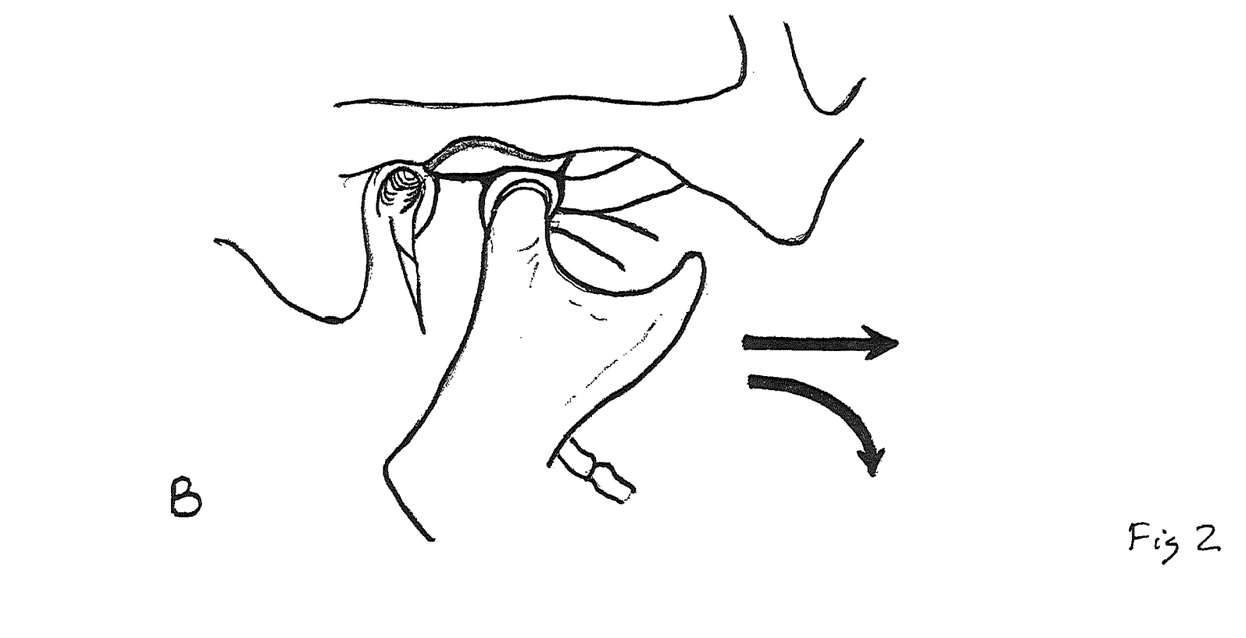
FIG. 2 is a side view of a mandible.

This mechanical device will have different components. Extension arms on each side will have ability to adjust height sufficient to reach each patient's angle of jaw. The extension arms will be foldable, so they will be out of the way once done with their job. The distance between them is easily changed, so they could be moved towards each other for smaller size patient and moved away from each other for larger size patient. Each arm will have a detachable and thus disposable 'mandible rest,' which is a cushioned seat for resting the angle of the mandible. A replaceable H-shaped belt is oriented with the bridge of the H to rest on the chin. Both the upper arms will be adjustable with end attachments just below the mandible rest. Both lower arms will be non-elastic or even not flexible and will have end attachments at the base of the extension arms. Thus, as the mandible rest is being elevated to reach patients' angle of mandible, patients' chin will tilt to open the mouth (due to the non-flexible arms of H-belt pulling the chin down). Hence the invention biases the mandible towards the natural movements of extension combined with opening rotation—as shown in FIG. 2—in the same manner as the manual prior art Jaw Thrust maneuver.

Both the extension arms and H-belt will be mounted on a backboard that can be easily placed underneath the patient's head, thus making it easy to move in and out depending on patient's need. The board will have a groove between the extension arms; so that distance between the arms can be changed (they can be moved towards or away from each other depending on patients' size). This board may be equipped with inflatable cuffs/pillows (either manual or automatic) that could provide for the roll under the shoulder used for airway support of infants and children under the age of 2 years. Another inflatable pillow could be positioned to provide head rest for older children and adult.

The invention advantageously frees up a rescuer who could perform other functions. This will avoid unnecessary fatigue of the rescuer if jaw thrust/chin tilt has to be done for longer duration. As the jaw is well supported on the mandible rest, it may maintain the head in the midline. The inflatable pillow for shoulder or head will help align the airway further depending on the age of the patient. The invention will be used by an EMT during transport of unconscious patient and emergency physicians, anesthesiologists, and intensivist can use it for sedated, post-operative or unconscious patient to open and maintain the airway.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 3:
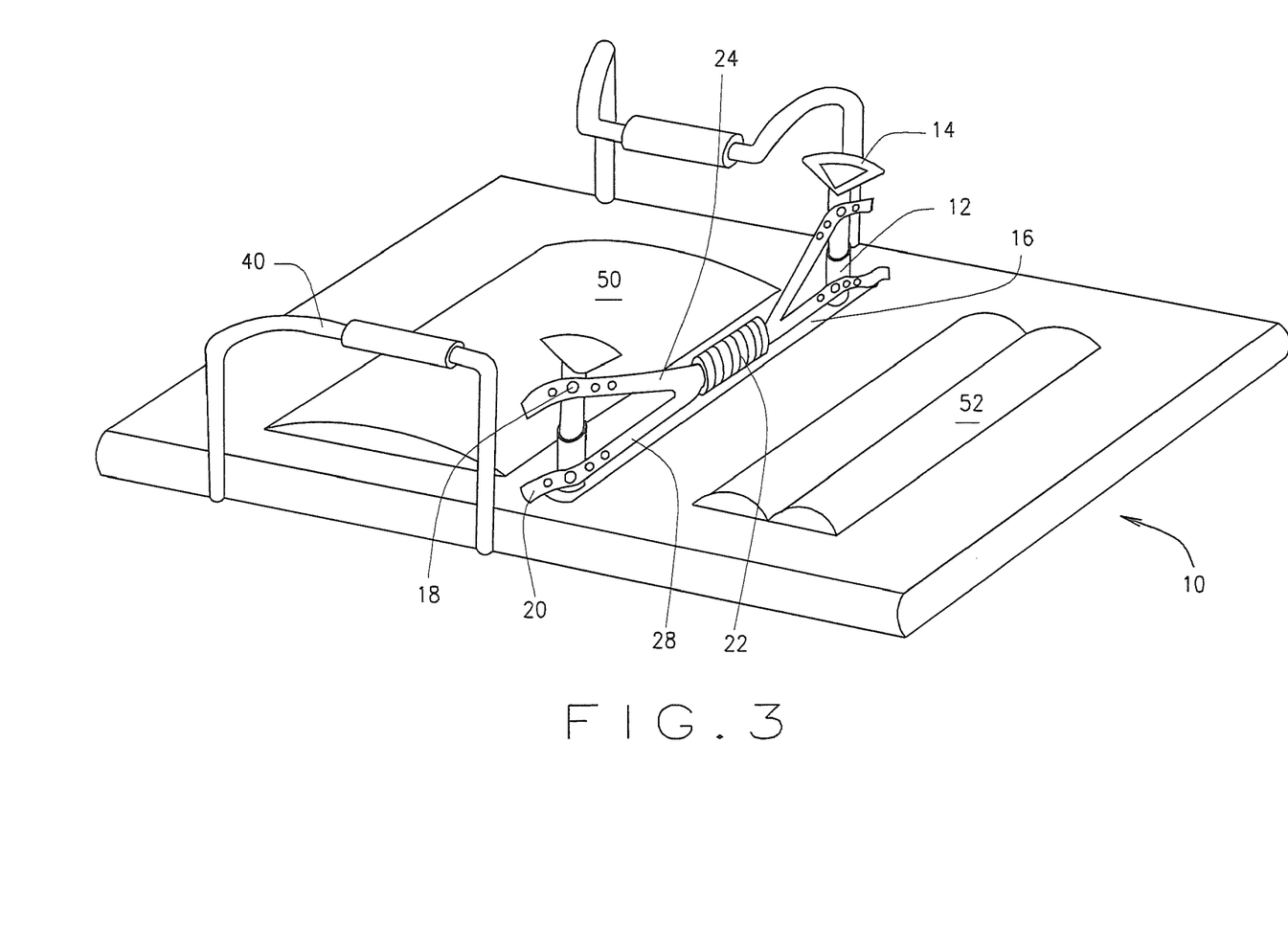
FIG. 3 is a perspective view of the jaw thrust mechanism.

FIG. 3 is a perspective view of the present invention. The components are mounted on a base, which in the depicted embodiment is a backboard 10 or a panel that may be fixedly attached to a pre-existing backboard, serves as a platform for mounting the various features of the present invention. A pair of telescoping extension arms 12 are mounted on either side of the backboard 10, on an upper surface facing a patient.

These extensions 12 may slide medially and laterally, in order that they may be moved closer or farther away from the patient's mandible, thus allowing a firm engagement of the mandible rests 14, which are mounted on top of the telescoping extensions 12. In the depicted embodiment, medial and lateral translation of the extending arms 12 is achieved by mounting the extending arms 12 within a groove 16. The extending arms telescope vertically in order that the mandible rests 14 may again be put in engagement with a dorsal aspect of a patient's mandible, bilaterally.

Attached to an upper portion 18 and a lower portion 20 of the extending arms 12 are straps or bands. The straps are joined in a center portion 22 which comprises a chin strap. In the depicted embodiment the chin strap includes a pad. An upper strap 24 is attached to an upper portion 18 of each extending arm 12, bilaterally. A lower portion 28 of the strap is attached to a fixed lower portion 20 of the extendible arms 12, bilaterally. The lower straps 28 are not extendable. They may be adjusted to the patient's size initially, but during the jaw thrust maneuver and thereafter they do not flex or extend. In the depicted embodiment, straps 28 are non-elastic fabric straps. They have a series of holes for initial adjustment. The fixation of the straps to separate portions of the telescoping extension arm assure that the ends of straps 28 will be separated from the ends of straps 24 when the mandible rests are elevated and the thrust maneuver is executed.

Supplemental features of the present invention in the depicted embodiment include side bars 40 for stabilizing the patient's head. The side bars 40 may be moved in and out of position by rotation or translation towards and away from the sides of the patient's head. Also shown in the depicted embodiment are pillows 50 and 52. These pillows are designed to be extended and retracted vertically in any manner, as for example by inflation, as in the depicted embodiment. The first pillow 50 is for use with adult patients, who typically have bulkier shoulders and optimally have a straight spine and airway maintained by elevating the head relative to the body. Conversely, children have larger heads proportional to their body size. Accordingly, the best technique for maintaining a straight spine and airway in children is by elevating their shoulders. For this purpose a second pillow 52 is placed below the chin strap assembly. Optionally, the pillows may be adjustable towards the patient's head or feet in order to best position the patient's head.

In use, a patient is placed on the backboard 10, the side bars 40 and one of the pillows 50 or 52 are adjusted to the patient's head and shoulders. Thereafter, the extending arms 12 are translated medially or laterally in order to approximate the mandible rests 14 to a dorsal aspect of the patient's mandible. The chin strap 22 is put on and slightly above the patient's chin, below the lower lip. Thereafter the extendible arms 12 are telescopically extended so that the mandible rests exert pressure on the patient's mandible, forcing it upwards such that the mandible advances outwards relative to the patient's maxilla. The chin strap 22, being non-extendibly anchored to the lower extension member 20, will be restrained relative to the upward pressure on the mandible rests 14, and accordingly be forced by the upwards pressure to move in the only available direction, which is to rotate downwards and away from the patient's maxilla, thereby achieving the desired opening of the jaw and airway beneath it. Once the desired degree of extension and opening of the patient's jaw has been achieved, it may be maintained in that position by upward pressure of the mandible rests 14 and rotational pressure of the chin strap 22 in turn being maintained by locking the extending arms 12 in their telescoped, extended position. This may be achieved by any known means. As for example, selective insertion of a locking pin, tightening of a set screw or a ratchet. Once set, the user may let go of the jaw thrust device of the present invention and proceed to other medical care and the patient's airway will be advantageously maintained in the open jaw thrust position by the device without further support from any medical practitioner.

FIGS. 4-7 refer to an alternate embodiment of the present invention. This embodiment is comprised generally of a platform 110 which may be a portion of a backboard or a plate attachable to a backboard. Mounted on the plate 110, generally, are a first side bar assembly 140A and a second side bar assembly 140B, corresponding respectively to the patient's left and right side. These side bar assemblies may be used as head stabilizers, head positioners and/or head rest. The second embodiment also is comprised of a first mandible rest assembly 108A and a second mandible rest assembly 108B corresponding to a patient's left side and a patient's right side, respectively. Finally, a chin strap 122 is non-elastically attached to the plate 110 at attachment 120, which may be a buckle, such as a cam buckle, although other adjustment members may be used. In the illustrated embodiment, attachment 120 is located below the vertical adjustment member 112. Alternatively, chin straps may be mounted with four anchors, with extra substantially symmetrical anchors 121 being positioned higher than the first anchors 120, for example between the side bar and mandible rest assemblies.

Each of the head stabilization assemblies 140 is mounted on a transverse slot 142. The head stabilization/immobilization assemblies each include a base block 144 and a vertical adjustment element 146 which may, as depicted, be a vertical rod. The head stabilization assemblies 140 may be adjusted medially and laterally by sliding them in and out along the slots 142. They may be fixed in a user selected position by application of a fixating device (not shown) as for example a set screw. These assemblies may be used to immobilize the head, for example in the midline of the overall plate and back board.

Figure 4:
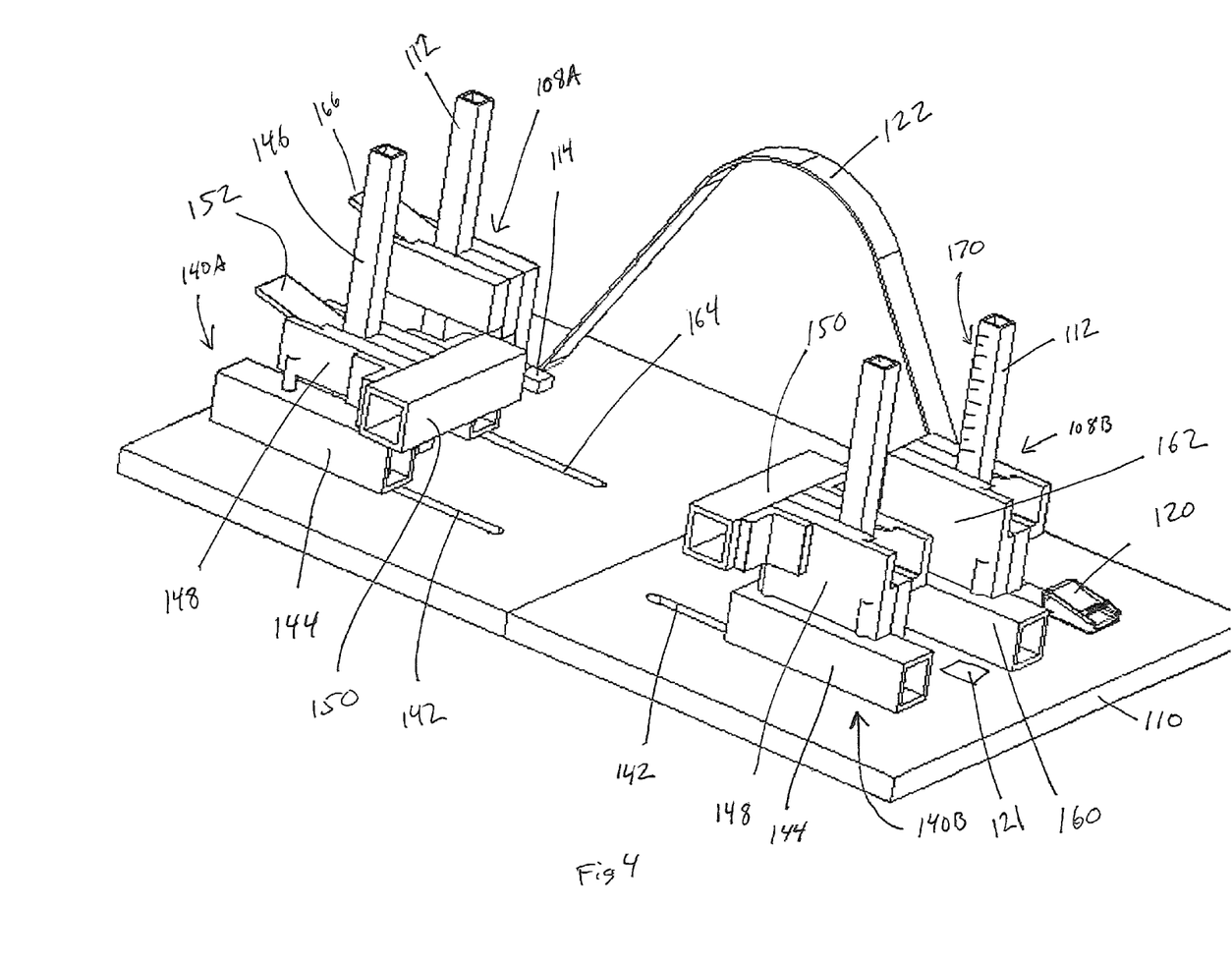
FIG. 4 is a perspective view of an alternate embodiment in a first position.
Figure 5:
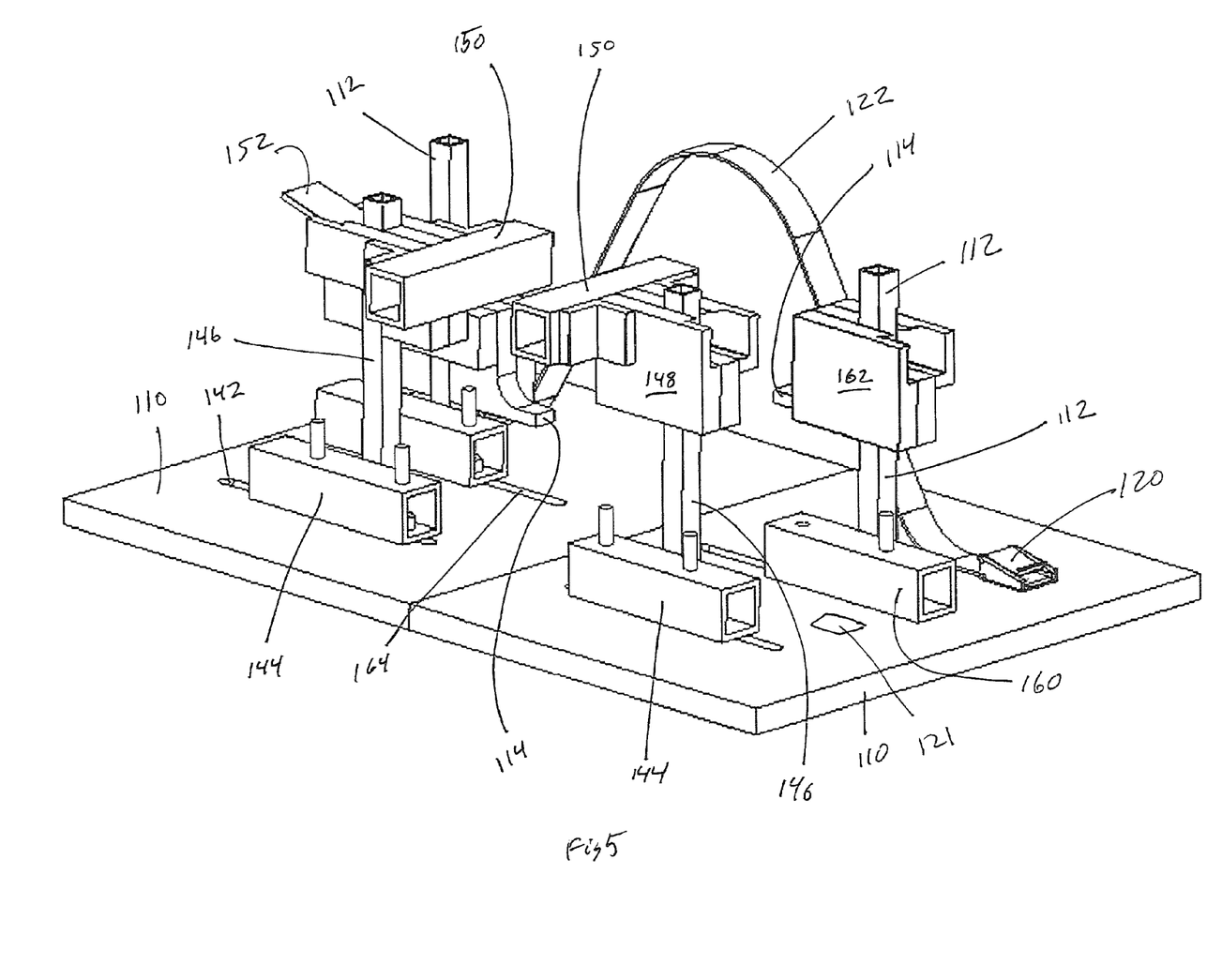
FIG. 5 is a perspective view of the alternate embodiment in a second position.
Figure 6:
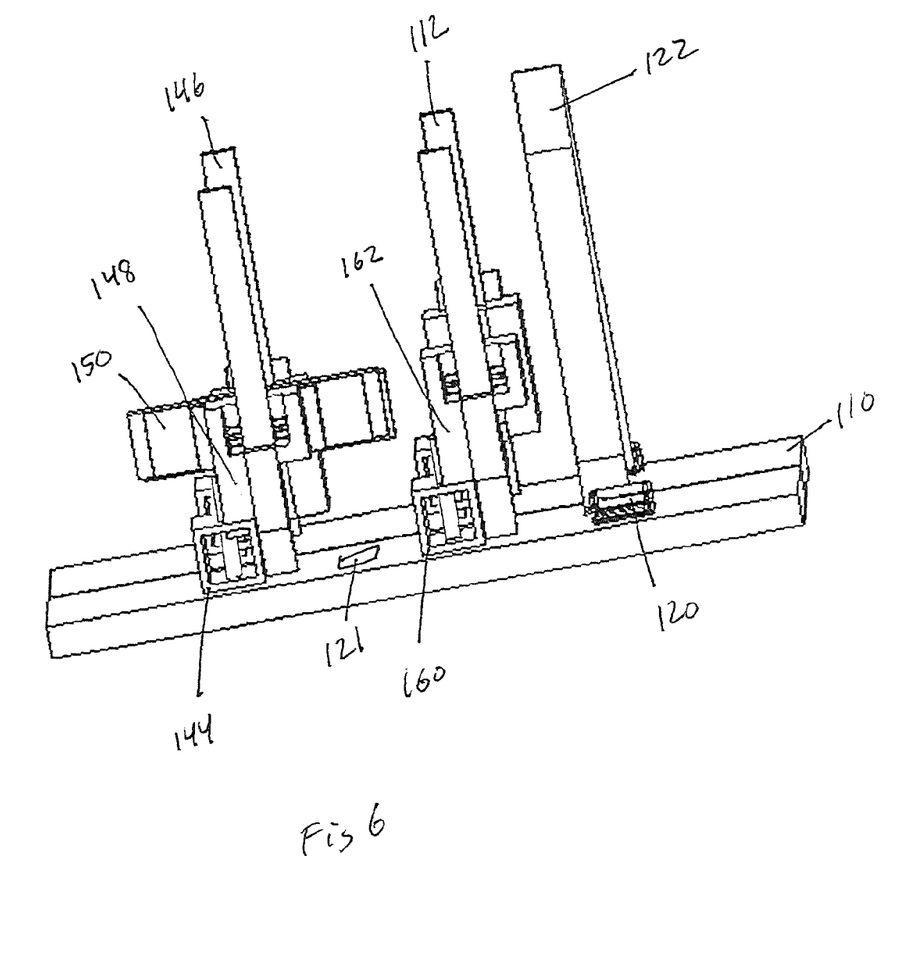
FIG. 6 is a side view of the alternate embodiment.
Figure 7:
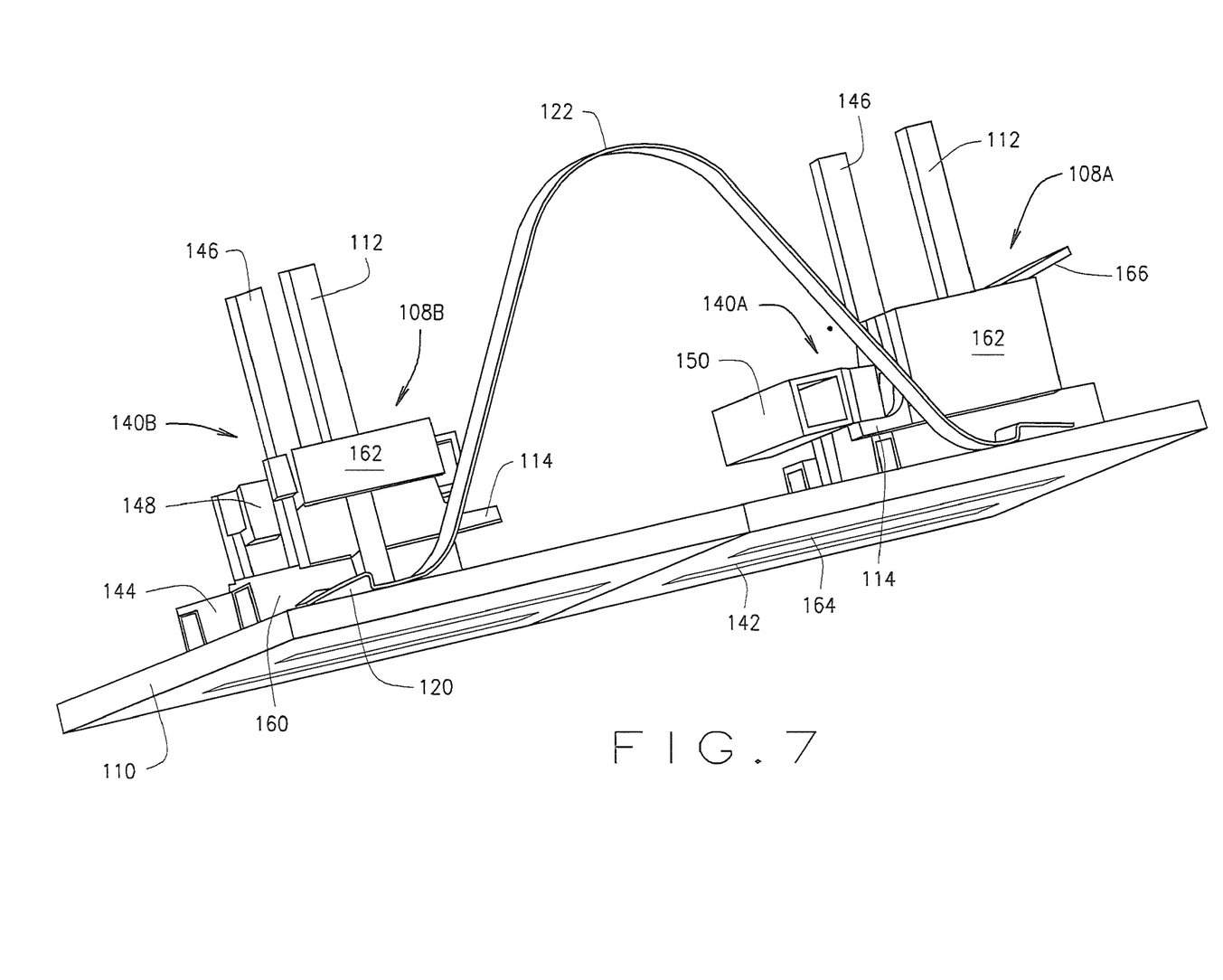
FIG. 7 is a perspective view of the alternate embodiment.

Each head stabilization assembly 140 has a vertical riser block 148. Vertical riser blocks have mounted to them head rest blocks 150. The vertical riser blocks 148 and head rest 150 may be raised and lowered by sliding along the vertical rods 146. When raised or lowered to a user selected position they may be locked in placed by application of a locking device which may be, as depicted a tensioning lever 152. The head rests 150 are located at a user selected position on the patient's head, for example, at the temple, so that the patient's head may be advantageously stabilized both in keeping with the general medical principal that some patients' injuries should be treated with head stabilization and also so that the head may be stabilized for application of the mandible engagement assemblies 108. FIG. 4 depicts the head stabilization assemblies 140 in a first position that is a beginning position. The beginning position is laterally spaced away from the patient and the head rests 150 are lowered. FIG. 5 depicts both head stabilization assemblies 140 in a position to stabilize the patient's head; that is, each has been moved medially to a position where the patient's head may be engaged and each head rest 150 has been raised to a position selected by the user to best stabilize the patient's head, for example at the temple.

Mandible rest assemblies are similar to the head stabilization assemblies in their adjustment mechanisms. The mandible rest assemblies also include a base block 160 and a riser 162. The mandible rest themselves 114 are mounted on the risers 162 and extend medially inwards towards the patient and the patient's mandible. The mandible rest assemblies 108 also each slide medially and laterally along a slot 164 and may be locked in a user selected position by means of a fixating element (not shown) such as for example a set screw. The mandible rests (and head rests 150) may include cushions or pads for patient comfort. The pads may be removable for cleaning. The riser 162 may be raised and lowered along the vertical adjustment member 112, which may be, as depicted, a vertical rod. When a user selected position of the mandible rest 114 has been reached, the mandible rest may be locked into position by a locking device, as for example in a depicted embodiment a torsion lever 166. In this manner, the mandible rest 114 may be placed approximate to the dorsal aspect of the patient's mandible, that is the back of the jaw closest to the back plate 110, and thereafter raised by raising the risers 162 along the vertical element 112. The consequent lifting pressure on the patient's mandible will execute the advantageous maneuver of a jaw thrust.

The force applied for a therapeutic jaw thrust may be in the range of from 2 to 18 pounds, and preferably about 8 pounds. Accordingly, components should be of sufficient strength to support and maintain such amounts of force. The vertical rods may be of sufficient height to maintain component positions exerting these force ranges on the patient, for example up to about 10 inches high for pediatric use. Materials for components may be any material capable of maintaining these forces, including for example plastics, fiberglass or metal such as stainless steel.

Figure 8:
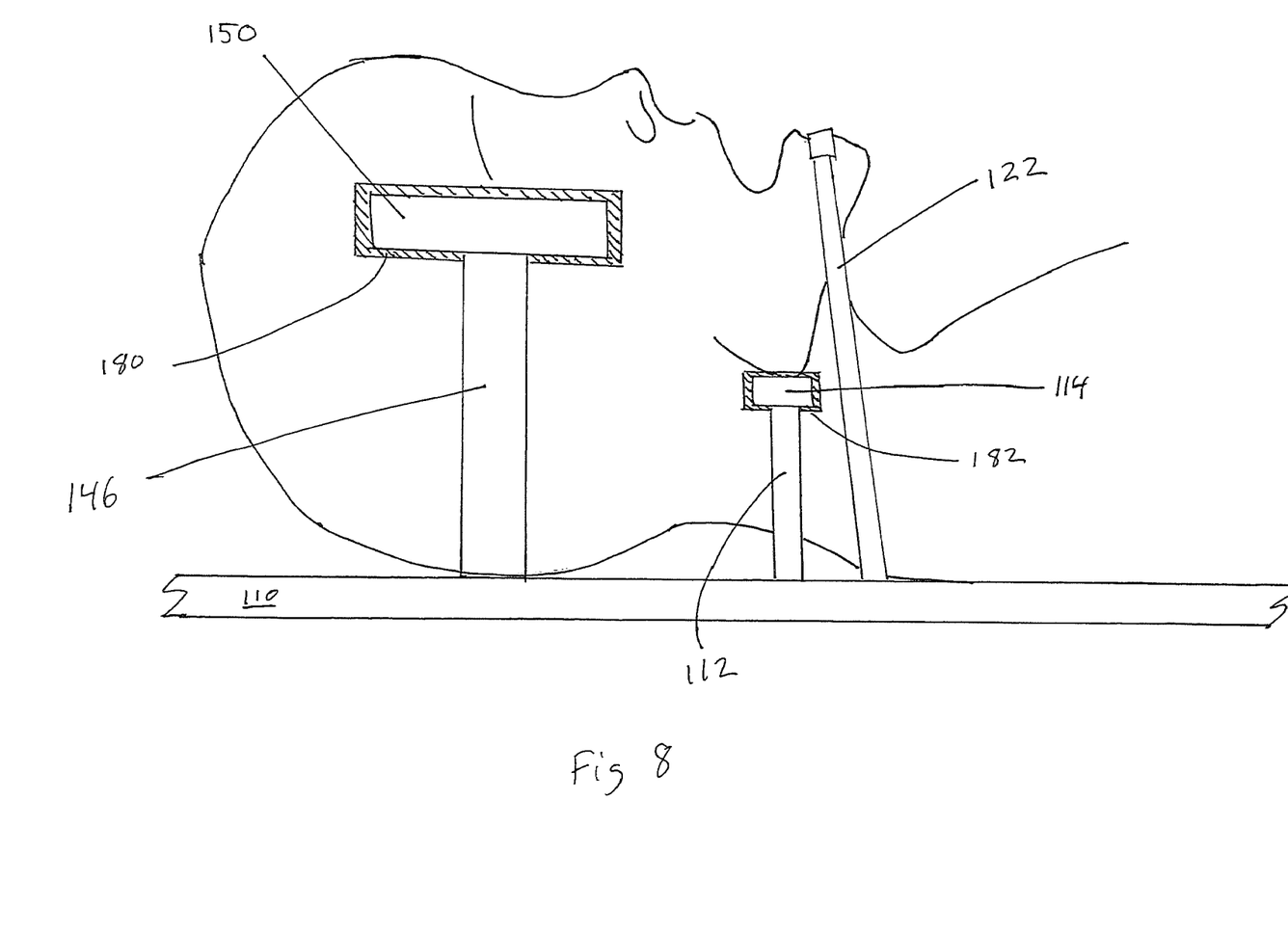
FIG. 8 is a schematic view of the alternate embodiment in use.

In operation, a patient is placed on a backboard (not shown) which has the plate 110 either incorporated integrally into it or attached to it. As seen in FIG. 8, the patient's head is placed between the head support assemblies 140 and the mandible rest assemblies 108. The head support assemblies 140 are moved medially and the head rest 150 are raised until stabilizing contact is made with the patient's head. Then adjustment locks such as for example set screws and the torsion levers 152 are set so that the head stabilization assemblies 140 are locked into position in engagement with the patient's head, immobilizing it. Thereby, the patient's head is stabilized in a manner advantageous for both general medical purposes, as for example in stabilizing the head of a suspected neck injury victim or multiple trauma victim, and for purposes of executing a jaw thrust to maintain a patent airway. Thereafter the chin strap 122, which is non-elastic, is placed over the patient's chin and the length of the strap 122 is appropriately adjusted for the healthcare provider with adjustment means such as for example a buckle 120. In the illustrated embodiment 122 is advantageously anchored below the patient's glenoid fossa. Next, the mandible adjustment assemblies 108 are each slid medially towards the patient's neck and mandible until the mandible rest 114 are engaged with the mandibular ramus, i.e., the back or dorsal aspect of the patient's mandible. Thereafter the risers 162 are elevated and slid along the vertical adjustment element 112 away from the back plate 110. In so doing, the healthcare provider using the apparatus will execute the advantageous jaw thrust maneuver. Simultaneously with elevation away from the back plate 110 of the patient's mandible, the chin strap will prevent the ventral aspect of the patient's mandible, i.e., his chin, from rising with the rest of the mandible. The chin will accordingly move in the only direction available for it to move, which is to rotate away from the patient's maxilla towards the patient's chest. Thus, the upward movement of the mandible rest 114 and the consequent rotation affected by the restraint of the chin strap 122, will automatically and advantageously execute the jaw thrust maneuver for maintaining a patient's airway. In order to aide in symmetrical application of all risers, the vertical members may include hash marks and/or calibrations 170.

After use removable cushions or pads 180 and 182 may be removed and either cleaned or disposed of and replaced. Other components may be cleaned after the pads are removed.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A jaw-thrust device comprising:
a base;
a mandible rest adapted to be mounted in a position proximate to a patient's mandible;
an extension apparatus, said extension apparatus being mounted on said base, said extension apparatus supporting said mandible rest;
said extension apparatus being vertically extendable to move said mandible rest through jaw thrusting motion which biases the patient's mandible towards a natural movement of extension of the mandible;
side bars, said side bars being mounted to deploy proximate to a patient's head, said deployment adapted to immobilize the patient's head;
a chin pad;
at least one strap, said at least one strap connecting said chin pad to at least one of said base or said extension apparatus and said at least one strap being non-extendible, said at least one strap being anchored to said base or said extension apparatus by at least one anchor adapted to be located at or below a patient's glenoid fossa;
whereby said mandible rest is adapted to receive jaw thrusting pressure caused by said jaw thrusting motion and responsively cause rotational force on said chin pad, thereby rotating a patient's chin away from a patient's maxilla, causing a patient's mouth to move to an open position without substantially tilting the patient's head.

2. The jaw-thrust device of claim 1 further comprising a head rest and a head rest extension apparatus.

3. The jaw-thrust device of claim 2 further comprising a pad on said head rest.

4. The jaw-thrust device in claim 2 further comprising a connector being anchored to said base or said extension apparatus by at least one anchor located at or below said extension apparatus.

5. The jaw-thrust device of claim 1 wherein a connector is said at least one strap.

6. The jaw-thrust device of claim 5 wherein said connector is four straps.

7. The jaw-thrust device of claim 1 further comprising extension arms that are further comprised of a base portion and an extending portion.

8. The jaw-thrust device of claim 7 wherein a connector is attached to said base portion of each of said extension arms.

9. The jaw-thrust device in claim 1 wherein the jar-thrust device is adapted to maintain an open airway unattended.

10. The jaw-thrust device of claim 1 wherein said extension apparatus comprises a pair of telescopic extension arms.

11. The jaw-thrust device of claim 1 further comprising at least one of a head pillow or a shoulder pillow.

12. The jaw-thrust device of claim 1 wherein extension arms are adjustable along a medial to lateral axis relative to said patient.

13. The jaw-thrust device of claim 1 wherein said mandible rest is on a riser, said riser being slideably mounted on a shaft, said shaft being substantially perpendicular to said base.

14. The jaw-thrust device of claim 1 wherein application of said mandible rest proximate to the patient's mandible is adapted to be proximate to a patient's mandible ramus.

15. The jaw-thrust device of claim 1 wherein said extension apparatus is comprised of two extension apparatuses, said two extension apparatuses being adapted to be disposed on each said of the patient's head.

16. The jaw-thrust device of claim 1 wherein said extension apparatus has hash marks, said hash marks indicating a height of an extending portion of said extension apparatus.

17. The jaw-thrust device of claim 1 further comprising a pad on said mandible rest.

18. The jaw-thrust device of claim 1 further comprising a pad on said mandible rest being removable.

19. The jaw-thrust device of claim 1 further comprising two head rests, said two head rests being adapted to be deployed on either side of the patient's head and adjustable to immobilize the patient's head.

20. The jaw-thrust device of claim 1 further comprising a head pillow and a shoulder pillow.

\* \* \* \* \*